(12) United States Patent
Diaz Martin et al.

(10) Patent No.: US 7,833,999 B2
(45) Date of Patent: Nov. 16, 2010

(54) TETRAHYDROISOQUINOLINE SULFONAMIDE DERIVATIVES, THE PREPARATION THEREOF, AND THE USE OF THE SAME IN THERAPEUTICS

(75) Inventors: Juan Antonio Diaz Martin, Madrid (ES); Maria Dolores Jimenez Bargueno, Alcobendas (ES)

(73) Assignee: sanofi-aventis, Paris (FR)

( * ) Notice: Subject to any disclaimer, the term of this patent is extended or adjusted under 35 U.S.C. 154(b) by 970 days.

(21) Appl. No.: 11/559,929

(22) Filed: Nov. 15, 2006

(65) Prior Publication Data

US 2007/0105834 A1    May 10, 2007

Related U.S. Application Data

(63) Continuation of application No. PCT/FR2005/001279, filed on May 24, 2005.

(30) Foreign Application Priority Data

May 25, 2004   (FR) .................................. 04 05607

(51) Int. Cl.
*C07D 403/02* (2006.01)
*A61K 31/496* (2006.01)
(52) U.S. Cl. .............................. 514/210.21; 514/232.8; 514/253.05; 514/307; 544/128; 544/363; 546/139; 546/148
(58) Field of Classification Search ............... None
See application file for complete search history.

(56) References Cited

U.S. PATENT DOCUMENTS

| 5,602,145 | A | 2/1997 | Samanen |
| 5,798,352 | A | 8/1998 | Danilewicz |
| 7,678,807 | B2 | 3/2010 | Diaz Martin et al. |
| 2008/0261999 | A1 | 10/2008 | Martin |

FOREIGN PATENT DOCUMENTS

| EP | 1 070 714 A1 | 1/2001 |
| EP | 1 679 309 A1 | 7/2006 |
| WO | WO 00/71507 A2 | 11/2000 |
| WO | WO 02/053558 | 7/2002 |
| WO | WO 02/076925 | 10/2002 |
| WO | WO 03/055848 | 7/2003 |
| WO | WO 03/076527 A1 | 9/2003 |
| WO | WO 2004/019935 | 3/2004 |
| WO | WO 2005/035514 A2 | 4/2005 |
| WO | WO 2006/018308 | 2/2006 |
| WO | WO 2006/018309 | 2/2006 |

OTHER PUBLICATIONS

West, Anthony R., Solid State Chemistry and its Applications, Wiley, New York, 1988, pp. 358 & 365.*
Korte, et al, Characterization and tissue Distribution of H3 Histamine Receptors in Guinea Pigs by Nalpha-Methylhistamine, Biochemical and Biophysical Research Communications, (1990) 168(3), pp. 979-986.
Lovenberg, et al, Cloning of Rat Histamine H3 Receptor Reveals Distinct Species Pharmacological Profiles, JPET (2000) 293, pp. 771-778.
Tozer, et al, Histamine H3 Receptor Antagonists, Exp. Opin. Ther. Patents (2000) 10(7), pp. 1045-1055.
West, et al, Identification of Two H3-Histamine Receptor Subtypes, Molecular Pharmacology, 38, pp. 610-613, 1990.
Grunewald et al, Examination of the Role of the Acidic Hydrogen in Imparting Selectivity of 7-(Aminosulfonyl)-1,2,3,4-tetrahydroisoquinoline (SK&F 29661) Toward Inhibition of Phenylethanolamine N-Methyltransferase vs the alpha2-Adrenoceptor, J. Med. Chem., 1997 (40) pp. 3997-4005.
Katritzky et al, 2-Substituted-1,2,3,4-tetrahydroisoquinolines and chiral 3-carboxyl analogues from N-benzotriazolylmethyl-N-phenethylamines, Tetrahedron: Asymmetry, 2001 (12) pp. 2427-2434.
Liu et al, Does the [3H]Mepyramine Binding Site Represent the Histamine H1 Receptor? Re-examination of the Histamine H1 Receptor with Quinine, JPET, 1994 (268) 2, pp. 959-964.
Vippagunta et al., Crystalline solids, Advanced Drug Delivery Reviews, 2001 (48), pp. 3-26.

\* cited by examiner

*Primary Examiner*—Zinna N Davis
(74) *Attorney, Agent, or Firm*—Kelly L. Bender; Irving Newman

(57) ABSTRACT

The invention relates to tetrahydroisoquinoline sulfonamide compounds (of formula (1) as defined in the specification), their preparation and their use in therapies for the treatment of central nervous system diseases such as vigilance and sleep disorders, narcolepsy, Alzheimer's disease and other dementias, Parkinson's disease, attention disorders in hyperkinetic children, memory and learning disorders, epilepsy, schizophrenia, moderate cognitive disorders, depression, anxiety, sexual dysfunction, dizziness and travel sickness.

19 Claims, No Drawings

TETRAHYDROISOQUINOLINE SULFONAMIDE DERIVATIVES, THE PREPARATION THEREOF, AND THE USE OF THE SAME IN THERAPEUTICS

CROSS-REFERENCE TO RELATED APPLICATIONS

This application is a continuation of PCT/FR2005/001279, filed May 24, 2005, which claims priority from FR Patent Application No. 04,05,607, filed May 25, 2004.

SUMMARY OF THE INVENTION

The present invention relates to sulfonamide derivatives, to the preparation thereof and to the therapeutic use thereof, in particular in the treatment of disorders that are improved by modulation of the histamine $H_3$ receptor, such as obesity, diabetes and central nervous system diseases such as vigilance and sleep disorders.

DETAILED DESCRIPTION OF THE INVENTION

Consequently, a first subject of the present invention is the compounds corresponding to formula I

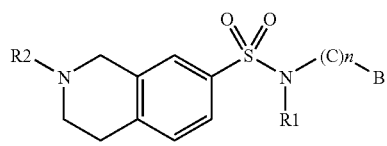

I in which:
  n can represent a value between 1 and 6;
  —(C)n- represents a —$C_{1-6}$ alkylidene group optionally substituted with 1 to 4 substituents chosen from a halogen atom, and a hydroxyl, nitro, cyano, amino, $C_{1-3}$ monoalkylamino, $C_{2-6}$ dialkylamino or $C_{1-3}$ alkoxy group;
  R1 represents
    a hydrogen atom,
    a $C_{1-6}$ alkyl group;
  R2 represents
    a hydrogen atom,
    a $C_{1-6}$ alkyl or $C_{3-6}$ cycloalkyl group optionally substituted with 1 to 4 substituents chosen from a halogen atom, a hydroxyl, nitro, cyano, amino, $C_{1-3}$ monoalkylamino, $C_{2-6}$ dialkylamino, $C_{1-2}$ perhaloalkyl, $C_{1-3}$ haloalkyl, $C_{1-3}$ alkoxy or $C_{3-6}$ cycloalkyl group, a monocyclic heteroaryl such as a thienyl, furyl or pyrrolyl, or an aryl, such as a phenyl or a naphthyl; the aryl being optionally substituted with 1 to 4 substituents chosen from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl or $C_{1-3}$ alkoxy group or a $C_{1-3}$ alkylidenedioxy group;
  B represents
  NR3R4,
    R3 and R4 represent, independently of one another, a $C_{1-6}$ alkyl group, or a hydrogen atom; or
    R3 and R4 together represent a $C_{1-6}$ alkylidene group, a $C_{2-8}$ alkenylidene group, a $C_{1-3}$ alkylidene-O—$C_{1-3}$ alkylidene group, or a $C_{1-3}$ alkylidene-N(R5)—$C_{1-3}$ alkylidene group where R5 represents a hydrogen atom, or a $C_{1-3}$ alkyl or $C_{1-6}$ alkylcarbonyl group, it being possible for these $C_{1-3}$ alkyl and $C_{1-6}$ alkylcarbonyl groups to be substituted with a halogen atom, or a hydroxyl, $C_{1-3}$ alkoxy, nitro, cyano or amino group; or
    an aminocycle, linked via a carbon to the group —NR1—(C)n-, such as aziridine, azetidine, pyrrolidine, piperidine or morpholine;
  the groups R3 and R4 and also the aminocycle being optionally substituted with 1 to 4 substituents chosen from a phenyl, a benzyl, a halogen atom, and a hydroxyl, nitro, cyano, amino, $C_{1-3}$ monoalkylamino, $C_{2-6}$ dialkylamino, $C_{1-3}$ alkyl or $C_{1-3}$ alkoxy group; and the nitrogen atom optionally substituted with a $C_{1-3}$ alkyl.

In the context of the present invention, the term:
  "$C_{x-z}$" is intended to mean a carbon-based chain that may contain from x to z carbon atoms; for example, $C_{1-3}$ indicates a carbon-based chain that may contain from 1 to 3 carbon atoms;
  "alkyl" is intended to mean a linear or branched, saturated aliphatic group; for example, a $C_{1-4}$ alkyl group represents a linear or branched, saturated carbon-based chain containing from 1 to 6 carbon atoms, more particularly a methyl, ethyl, propyl, isopropyl, butyl, isobutyl, tert-butyl, etc. radical; the term "$C_{x-y}$ alkylidene" denoting a divalent, linear or branched $C_{x-y}$ alkyl group; the term "$C_{2-8}$ alkenylidene" denoting a divalent, linear or branched, unsaturated $C_{x-y}$ alkyl group;
  "$C_{x-y}$ alkoxy" is intended to mean an alkyloxy group comprising a linear or branched, saturated aliphatic chain, containing x to y carbon atoms;
  "halogen atom" is intended to mean a fluorine, a chlorine, a bromine or an iodine;
  "$C_{1-3}$ monoalkylamino" is intended to mean an amino monosubstituted with a $C_{1-3}$ alkyl group;
  "$C_{2-6}$ dialkylamino" is intended to mean an amino disubstituted with two $C_{1-3}$ alkyl groups;
  "$C_{1-2}$ perhaloalkyl" is intended to mean a $C_{1-2}$ alkyl group in which all the hydrogen atoms are substituted with halogen atoms;
  "$C_{1-3}$ haloalkyl" is intended to mean a $C_{1-3}$ alkyl group in which at least one hydrogen atom is substituted with a halogen atom.

The compounds of formula I can contain one or more asymmetrical carbon atoms. They can therefore exist in the form of enantiomers or of diastereoisomers. These enantiomers and diastereoisomers, and also mixtures thereof, including racemic mixtures, are part of the invention.

The compounds of general formula I can be in the form of free bases or of addition salts with acids, which are also part of the invention. According to the present invention, these salts comprise those with pharmaceutically acceptable acids, but also those with inorganic or organic acids that allow a suitable separation or crystallization of the compounds of formula I. These salts can be prepared, according to methods known to those skilled in the art, for example, by reaction of the compound of formula I in the form of a base with the acid in an appropriate solvent, such as an alcoholic solution or an organic solvent, and then separation of the media that contains it by evaporation of the solvent or by filtration.

The compounds of formula I can also exist in the form of hydrates or of solvates, i.e. in the form of associations or combinations with one or more water molecules or with a solvent. Such hydrates and solvates are also part of the invention.

Furthermore, in the context of the present invention, the term "protective group Pg" is intended to mean a group that makes it possible, firstly, to protect a reactive function such as a hydroxyl or an amine during a synthesis and, secondly, to regenerate the intact reactive function at the end of synthesis. Examples of protective groups and also the methods of protection and deprotection are given in "Protective groups in Organic Synthesis $3^{rd}$ Ed.", Greene and Wuts (John Wiley & Sons, Inc., New York, 1999).

A subject of the present invention is also the compounds chosen from the following subgroups, in which:

n is equal to 2, 3 or 4; and/or

R1 represents a hydrogen atom or a $C_{1-2}$ alkyl group; and/or

R2 represents a hydrogen atom, or a $C_{1-4}$ alkyl or $C_{5-6}$ cycloalkyl group optionally substituted with 1 to 4 substituents chosen from a phenyl, and a $C_{3-6}$ cycloalkyl, $C_{1-2}$ perhaloalkyl, $C_{1-3}$ haloalkyl or $C_{1-3}$ alkoxy group; the phenyl being optionally substituted with 1 to 4 substituents chosen from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl or $C_{1-3}$ alkoxy group or a $C_{1-3}$ alkylidenedioxy group; and/or B represents

NR3R4,

R3 and R4 represent, independently of one another, a $C_{1-4}$ alkyl group; or when R3 and R4 together represent a $C_{1-6}$ alkylidene group, a $C_{2-8}$ alkenylidene group, a $C_{1-3}$ alkylidene-O—$C_{1-3}$ alkylidene group or a $C_{1-3}$ alkylidene-N(R5)-$C_{1-3}$ alkylidene group, B represents a group:

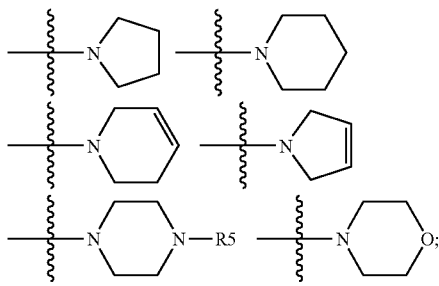

or an aminocycle linked via a carbon to the group —NR1-(C)n, such as aziridine, azetidine, pyrrolidine, piperidine or morpholine;

the groups R3, R4 and R5 and also the aminocycle being optionally substituted; and, more specifically, the subgroup where at the same time n, R1, R2 and B are as defined above.

More particularly, when B represents NR3R4 and R3 and R4 together form a $C_{1-6}$ alkylidene group, a $C_{2-8}$ alkenylidene group, a $C_{1-3}$ alkylidene-O—$C_{1-3}$ alkylidene group or a $C_{1-3}$ alkylidene-N(R5)-$C_{1-3}$ alkylidene group, or when B represents an aminocycle, then B is chosen from the following groups:

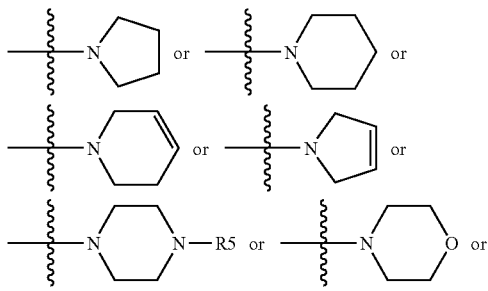

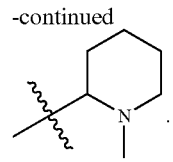

Another subject of the present invention concerns the following compounds:

1. N-[3-(diethylamino)propyl]-1,2,3,4-tetrahydroisoquinoline-7-sulfonamide;
2. (+/−)-N-[2-(1-methylpyrrolidin-2-yl)ethyl]-1,2,3,4-tetrahydroisoquinoline-7-sulfonamide;
3. N-[3-(diethylamino)propyl]-2-methyl-1,2,3,4-tetrahydroisoquinoline-7-sulfonamide;
4. N-[3-(diethylamino)propyl]-N-methyl-1,2,3,4-tetrahydroisoquinoline-7-sulfonamide;
5. 2-benzyl-N-[3-(diethylamino)propyl]-1,2,3,4-tetrahydroisoquinoline-7-sulfonamide;
6. 2-(cyclopropylmethyl)-N-[3-(diethylamino)propyl]-1,2,3,4-tetrahydroisoquinoline-7-sulfonamide;
7. 2-(cyclohexylmethyl)-N-[3-(diethylamino)propyl]-1,2,3,4-tetrahydroisoquinoline-7-sulfonamide;
8. (+/−)-N-[3-(2-methylpiperidin-1-yl)propyl]-1,2,3,4-tetrahydroisoquinoline-7-sulfonamide;
9. N-[3-(3,6-dihydropyridin-1(2H)-yl)propyl]-1,2,3,4-tetrahydroisoquinoline-7-sulfonamide;
10. N-[3-(diethylamino)propyl]-2-isopropyl-1,2,3,4-tetrahydroisoquinoline-7-sulfonamide;
11. N-[3-(diethylamino)propyl]-2-(2-thienylmethyl)-1,2,3,4-tetrahydroisoquinoline-7-sulfonamide;
12. N-[3-(diethylamino)propyl]-2-(3-thienylmethyl)-1,2,3,4-tetrahydroisoquinoline-7-sulfonamide;
13. N-[3-(2,5-dihydro-1H-pyrrol-1-yl)propyl]-1,2,3,4-tetrahydroisoquinoline-7-sulfonamide;
14. 2-cyclohexyl-N-[3-(diethylamino)propyl]-1,2,3,4-tetrahydroisoquinoline-7-sulfonamide;
15. (+/−)-2-(cyclohexylmethyl)-N-[2-(1-methylpyrrolidin-2-yl)ethyl]-1,2,3,4-tetrahydroisoquinoline-7-sulfonamide;
16. N-[3-(2,5-dihydro-1H-pyrrol-1-yl)propyl]-2-methyl-1,2,3,4-tetrahydroisoquinoline-7-sulfonamide;
17. N-[3-(4-benzylpiperazin-1-yl)propyl]-1,2,3,4-tetrahydroisoquinoline-7-sulfonamide;
18. N-(3-pyrrolidin-1-ylpropyl)-1,2,3,4-tetrahydroisoquinoline-7-sulfonamide;
19. N-(3-morpholin-4-ylpropyl)-1,2,3,4-tetrahydroisoquinoline-7-sulfonamide;
20. N-[3-(dimethylamino)propyl]-1,2,3,4-tetrahydroisoquinoline-7-sulfonamide;
21. 2-(cyclohexylmethyl)-N-(3-pyrrolidin-1-ylpropyl)-1,2,3,4-tetrahydroisoquinoline-7-sulfonamide;
22. (+/−)-2-(cyclopropylmethyl)-N-[2-(1-methylpyrrolidin-2-yl)ethyl]-1,2,3,4-tetrahydroisoquinoline-7-sulfonamide;
23. (+/−)-2-benzyl-N-[2-(1-methylpyrrolidin-2-yl)ethyl]-1,2,3,4-tetrahydroisoquinoline-7-sulfonamide;
24. (+/−)-2-(4-isopropylbenzyl)-N-[2-(1-methylpyrrolidin-2-yl)ethyl]-1,2,3,4-tetrahydroisoquinoline-7-sulfonamide;
25. (+/−)-2-(1,3-benzodioxol-5-ylmethyl)-N-[2-(1-methylpyrrolidin-2-yl)ethyl]-1,2,3,4-tetrahydroisoquinoline-7-sulfonamide;
26. (+)-N-[2-(1-methylpyrrolidin-2-yl)ethyl]-1,2,3,4-tetrahydroisoquinoline-7-sulfonamide;

27. (−)-N-[2-(1-methylpyrrolidin-2-yl)ethyl]-1,2,3,4-tetrahydroisoquinoline-7-sulfonamide;
28. (+)-2-(cyclohexylmethyl)-N-[2-(1-methylpyrrolidin-2-yl)ethyl]-1,2,3,4-tetrahydroisoquinoline-7-sulfonamide;
29. (−)-2-(cyclohexylmethyl)-N-[2-(1-methylpyrrolidin-2-yl)ethyl]-1,2,3,4-tetrahydroisoquinoline-7-sulfonamide;
30. (+/−)-2-(4-bromobenzyl)-N-[2-(1-methylpyrrolidin-2-yl)ethyl]-1,2,3,4-tetrahydroisoquinoline-7-sulfonamide
31. (+/−)-2-(2,5-dimethoxybenzyl)-N-[2-(1-methylpyrrolidin-2-yl)ethyl]-1,2,3,4-tetrahydroisoquinoline-7-sulfonamide
32. (+/−)-2-(2-methylbutyl)-N-[2-(1-methylpyrrolidin-2-yl)ethyl]-1,2,3,4-tetrahydroisoquinoline-7-sulfonamide
33. (+/−)-2-(3-methoxybenzyl)-N-[2-(1-methyl pyrrolidin-2-yl)ethyl]-1,2,3,4-tetrahydroisoquinoline-7-sulfonamide and
34. (+/−)-2-(3,5-dimethyl-benzyl)-N-[2-(1-methylpyrrolidin-2-yl)ethyl]-1,2,3,4-tetrahydroisoquinoline-7-sulfonamide.

A second subject of the present invention is processes for preparing the compounds of formula I according to the invention.

Thus, the compounds of formula I can be prepared according to the process represented in Scheme 1.

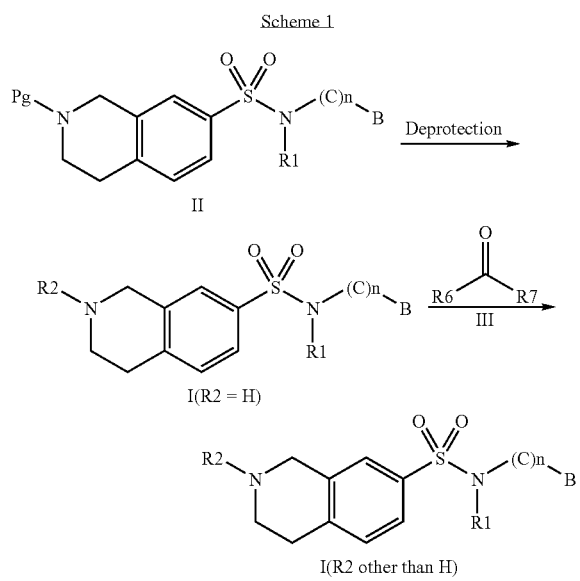

According to the process of Scheme 1, the compounds of formula I, in which R2 is other than a hydrogen atom, are prepared by amminative reduction, by reacting a secondary amine of formula I, in which R2 represents H, with an aldehyde or a ketone of formula III, where R6 and R7, after reaction, together form R2 as defined in formula I. The compounds of formula I where R2 represents a hydrogen atom can be obtained by deprotection of the compounds of formula II, according to conventional methods known to those skilled in the art. For example, the compounds of formula II, when Pg is a trifluoroacetyl group, can be deprotected in the presence of a base such as, for example, sodium carbonate, potassium carbonate, ammonia or barium hydroxide in a protic solvent, such as water or methanol or a mixture of these solvents, at a temperature between 0 and 100° C. Alternatively, the deprotection of the compounds of formula II, when Pg is a trifluoroacetyl group, can be carried out in the presence of an acid such as, for example, hydrochloric acid in a protic or aprotic solvent, such as water, methanol, ethanol or ethyl acetate or a mixture of these solvents, at a temperature between 0 and 100° C. Illustrations of the process are given in the examples.

The starting compounds of formula II can be prepared according to Scheme 2 or can be synthesized by conventional methods known to those skilled in the art.

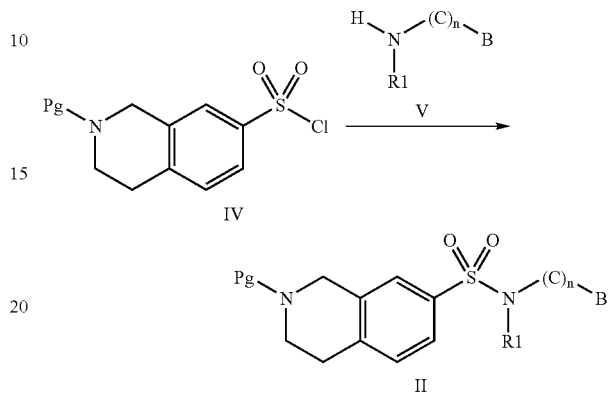

According to this scheme, the compounds of formula II, in which n, R1 and B are as defined in formula I, can be prepared by reaction of an amine of formula V, in which R1 and B are as defined in formula I, with a sulfonyl chloride of formula IV, in which Pg represents an appropriate protective group such as, for example, a trifluoroacetamide, so as to form a derivative of sulfonamide type of formula II, according to conventional methods known to those skilled in the art, for example, the reaction can be carried out in a protic or aprotic solvent, such as tetrahydrofuran, dichloromethane, ethyl acetate, N,N-dimethylformamide or acetonitrile or a mixture of these solvents, at a temperature of between 0 and 100° C., in the presence of a base such as, for example, potassium carbonate, sodium carbonate, diisopropylethylamine or triethylamine.

Alternatively, the compounds of formula II can be prepared by a Mitsunobu type reaction, according to Scheme 3.

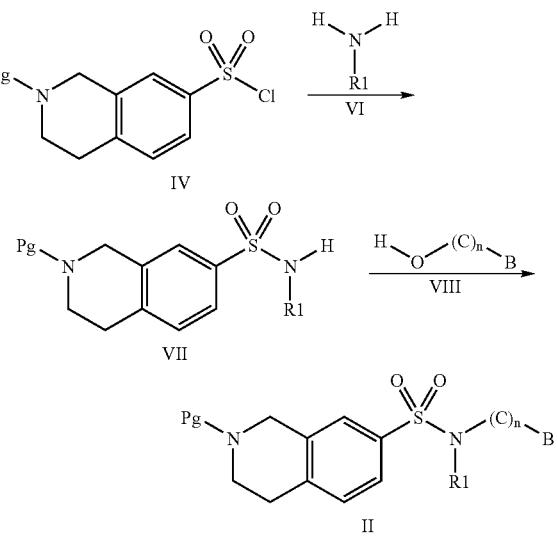

According to this alternative, a sulfonamide of formula VII, in which R1 is as defined in formula I, is reacted with an amino alcohol of formula VIII, in which n and B are as defined above. The reaction can be carried out conventionally in the presence of Mitsunobu reagents, such as an azo derivative, for example diethylazodicarboxylate, diisopropylazodicarboxylate, di-tert-butylazodicarboxylate, 1,1'-(azodicarbonyl)dipiperidine or N,N,N',N' tetramethylazodicarboxamide, and a phosphine, for example triphenylphosphine or tributylphosphine. The reaction can be carried out in an aprotic solvent, such as tetrahydrofuran or dioxane or a mixture of these solvents, at a temperature between 0 and 100° C., to give the compound of formula II. The sulfonamide of formula VII in which R1 is as defined in formula I can be prepared by reaction of an amine of formula VI, in which R1 is as defined in formula I, with a sulfonyl chloride of formula IV, in which Pg represents an appropriate protective group such as, for example, a trifluoroacetamide, according to conventional methods known to those skilled in the art, for example, the reaction can be carried out in a protic or aprotic solvent, such as tetrahydrofuran, dichloromethane, ethyl acetate, Ia N,N-dimethylformamide or acetonitrile or a mixture of these solvents, at a temperature between 0 and 100° C., in the presence of a base such as, for example, potassium carbonate, sodium carbonate, diisopropylethylamine or triethylamine.

The starting compounds IV and the amines of formulae V and VIII are directly commercially available, can be synthesized by conventional methods known to those skilled in the art, or are known in the literature.

For example, the diamines of formula V, in which n is equal to 3, can be prepared according to Scheme 4.

Scheme 4

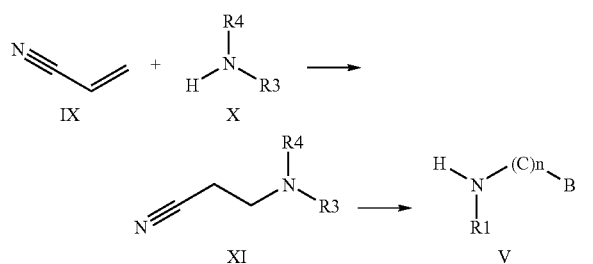

According to this process, the compounds of formula V, in which n is equal to 3, R1 represents a hydrogen atom and B represents an amine group, can be prepared by means of an addition reaction of an amine of formula X, in which R3 and R4 are as defined above, with the acrylonitrile of formula IX, so as to form a derivative of aminonitrile type of formula XI, according to conventional methods known to those skilled in the art, followed by reduction of the nitrile. The reduction can be carried out according to methods known to those skilled in the art, for example in the presence of diisobutylaluminum hydride at a temperature between −70° C. and 40° C. in an aprotic solvent such as dichloromethane or toluene or a mixture of these solvents; the reduction can also be carried out in the presence of a reducing agent, such as hydrogen, in the presence of a catalyst such as platinum, palladium or Raney nickel, in a solvent such as methanol or ethyl acetate, so as to give the compound of formula V, in which n is equal to 3, R1 represents a hydrogen atom and B represents an amine group. The compounds of formula V, in which R1 represents a $C_{1-6}$ alkyl group, can be prepared by alkylation of the compound of formula V obtained above, according to conventional methods known to those skilled in the art.

A subject of the present invention is also the compounds of formula II, when Pg represents a protective group or a hydrogen atom, as intermediates for the preparation of the compound of formula I.

The following examples illustrate the processes and techniques suitable for the preparation of this invention, without, however, limiting the scope of the claim.

EXAMPLE 1

N-[2-(1-Methylpyrrolidin-2-yl)ethyl]-1,2,3,4-tetrahydroisoquinoline-7-sulfonamide hydrochloride

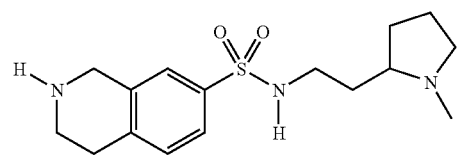

1.1-(+/−)-N-[2-(1-Methylpyrrolidin-2-yl)ethyl]-2-(2,2,2-trifluoroacetyl)-1,2,3,4-tetrahydroisoquinoline-7-sulfonamide hydrochloride A solution of 5.00 g (0.015 mol) of 2-(2,2,2-trifluoroacetyl)-1,2,3,4-tetrahydro-isoquinoline-7-sulfonyl chloride and 2.00 g (0.015 mol) of (+/−)-2-(1-methyl-pyrrolidin-2-yl)-ethylamine, in 50 ml of dichloromethane, is stirred overnight at ambient temperature. The solution is concentrated to dryness. The solid formed is purified by silica gel column chromatography, with a dichloromethane/methanol (97:3) mixture used as eluant, to give 4.30 g of the desired product in the form of a white solid.
Yield: 62%
Mp=amorphous 1.2-(+/−)-N-[2-(1-Methylpyrrolidin-2-yl)ethyl]-1,2,3,4-tetrahydroisoquinoline-7-sulfonamide hydrochloride A solution of 4.30 g (0.0094 mol) of 2-(2,2,2-trifluoroacetyl)-1,2,3,4-tetrahydroisoquinoline-7-sulfonamido-[2-(1-methylpyrrolidin-2-yl)ethyl] hydrochloride in 50 ml of methanol saturated with hydrogen chloride is heated for twelve hours at 60° C. The mixture is cooled and the solid that has formed is filtered off, washed with methanol and dried. 2.00 g of the desired product are obtained as a white solid.
Yield: (65%)
Mp=209-212° C.
$^1$H-NMR (DMSO-$d_6$)δ(ppm): 7.9 (1H, t), 7.7 (2H, d), 7.5 (1H, d), 4.3 (2H, s), 3.6 (5H, m), 3.1 (3H, m), 2.9 (2H, m), 2.7 (3H, m), 2.1 (1H, m), 1.9 (3H, m), 1.6 (2H, m) 2.7 (3H, s); 2.9 (2H, t).

1.3-(+) or (−)-N-[2-(1-Methylpyrrolidin-2-yl)ethyl]-1,2,3,4-tetrahydroisoquinoline-7-sulfonamide hydrochloride The compound obtained above in 1.2 is separated by chiral-phase preparative chromatography, to give its enantiomers. Specifically, the separation of 15.00 g of (+/−)-N-[2-(1-methylpyrrolidin-2-yl)ethyl]-1,2,3,4-tetrahydroisoquinoline-7-sulfonamide hydrochloride is carried out with a PROCHROM LC50 preparative HPLC system, with a CHIRALPACK AD stationary phase and a mobile phase formed from isohexane/ethanol/methanol (80%:10%:10%)+0.2% of diethylamine, to give 5.39 g of the dextrorotatory product, in the form of a white powder, with a chiral-phase enantiomeric purity of 99.67%, and 4.89 g of the levorotatory product, in the form of a white solid, with a chiral-phase enantiomeric purity of 99.48%. The two products are converted into their corresponding hydrochloride by a treatment with isopropanol saturated with hydrogen chloride.

Dextrorotatory enantiomer: Mp=114-117° C.; $[\alpha]_D^{20}$=+16 (c=0.5, methanol)

Levorotatory enantiomer: Mp=115-117° C.; $[\alpha]_D^{20}$=−16 (c=0.5, methanol)

EXAMPLE 2

(+/−)-2-(Cyclohexylmethyl)-N-[2-(1-methylpyrrolidin-2-yl)ethyl]-1,2,3,4-tetrahydroisoquinoline-7-sulfonamide oxalate (1:2)

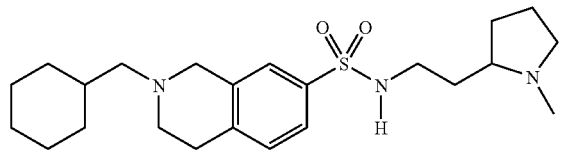

0.32 g (0.0003 mol) of palladium-on-charcoal at 10% is added to a solution of 2.02 g (0.0063 mol) of (+/−)-1,2,3,4-tetrahydroisoquinoline-7-sulfonamido-[2-(1-methyl-pyrrolidin-2-yl)ethyl] and 0.70 g (0.0063 mol) of cyclohexanecarboxaldehyde in 100 ml of methanol. The solution is hydrogenated for 24 hours in a Paar hydrogenator at a pressure of 45 Psi. The catalyst is removed by filtration and the filtered solution is evaporated to dryness. The crude oil obtained (2.90 g) is purified by silica gel column chromatography, with a dichloromethane/methanol (95:5) mixture used as eluant. The desired product (1.62 g; 62%) is obtained in the form of an oil.

The above oil is dissolved in 20 ml of ethanol, and then 0.77 g (0.0086 mol) of oxalic acid dissolved in 15 ml of ethanol is added. The precipitate is filtered off and washed with cold ethanol. 2.01 g of the desired product are obtained in the form of a white solid.

Yield: 86%
Mp=142-147° C.
$^1$H-NMR (DMSO-d$_6$)δ(ppm): 7.5 (2H, m), 7.29 (1H, m), 3.84 (2H, s), 3.35 (2H, m), 3.1 (1H, m), 2.9 (1H, m), 2.8 (2H, s), 2.7 (1H, m), 2.6 (3H, s), 2.5 (2H, m), 2.1-1.4 (13H, m), 1.15 (4H, m), 0.8 (2H, m).

EXAMPLE 3

(+)-2-(Cyclohexylmethyl)-N-[2-(1-methylpyrrolidin-2-yl)ethyl]-1,2,3,4-tetrahydroisoquinoline-7-sulfonamide oxalate (1:1.5)

According to a process similar to Example 2, with 1.00 g (0.0031 mol) of (+)-N-[2-(1-methylpyrrolidin-2-yl)ethyl]-1,2,3,4-tetrahydroisoquinoline-7-sulfonamide and 0.35 g (0.0031 mol) of cyclohexanecarboxaldehyde in 50 ml of methanol as starting product, 0.46 g of base is obtained, which base is converted into the corresponding sesquioxalate hydrate, as a white solid.

Yield: 20%
Mp=134-140° C.
$[\alpha]_D^{20}$=+12 (c=0.5, methanol)

EXAMPLE 4

(−)-2-(Cyclohexylmethyl)-N-[2-(1-methylpyrrolidin-2-yl)ethyl]-1,2,3,4-tetrahydroisoquinoline-7-sulfonamide oxalate (1:2)

According to a process similar to Example 2, with 1.00 g (0.0031 mol) of (−)-N-[2-(1-methylpyrrolidin-2-yl)ethyl]-1,2,3,4-tetrahydroisoquinoline-7-sulfonamide and 0.35 g (0.0031 mol) of cyclohexanecarboxaldehyde in 50 ml of methanol as starting product, 0.90 g of base is obtained, which base is converted into the corresponding dioxalate hydrate, as a white solid.

Yield: 27%
Mp=133-138° C.
$[\alpha]_D^{20}$=−8 (c=0.5, methanol)

EXAMPLE 5

2-Benzyi-N-[3-(diethylamino)propyl]-1,2,3,4-tetrahydroisoquinoline-7-sulfonamide oxalate (1:2)

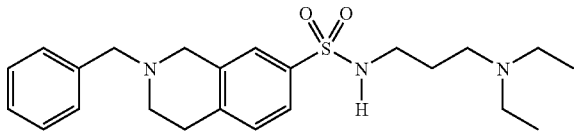

5.1-N-[2-(3-Diethylaminopropyl)-2-(2,2,2-trifluoro-acetyl)-1,2,3,4-tetrahydroisoquinoline-7-sulfonamide hydrochloride A solution of 1.00 g (0.0031 mol) of 2-(2,2,2-trifluoro-acetyl)-1,2,3,4-tetrahydroisoquinoline-7-sulfonyl chloride and 0.61 g (0.0047 mol) of N,N-diethyl-N-aminopropylamine in 25 ml of dichloromethane is stirred overnight at ambient temperature. The solution is concentrated to dryness and the oil formed is purified by silica gel column chromatography, with a dichloromethane/methanol (97:3) mixture used as eluant. 1.27 g are obtained.

Yield: 97%
Mp=Oil 5.2-N-[3-(Diethylamino)propyl]-1,2,3,4-tetrahydroisoquinoline-7-sulfonamide hydrochloride A solution of 5.39 g (0.013 mol) of N-[2-(3-diethylamino-propyl)-2-(2,2,2-trifluoroacetyl)-1,2,3,4-tetrahydroisoquinoline-7-sulfonamide hydrochloride, dissolved in 60 ml of methanol saturated with hydrogen chloride, is heated for twelve hours at 60° C. The mixture is cooled and the solid that has formed is filtered off, washed with methanol and dried. The residue is dissolved in an aqueous solution of sodium hydroxide. The aqueous phase is extracted several times with ethyl ether. The organic phases are combined and dried over anhydrous magnesium sulfate. The oil obtained (2.80 g) is used without additional purification.

Yield: 67%
Mp=Oil

5.3-2-Benzyl-N-[3-(diethylamino)propyl]-1,2,3,4-tetrahydroisoquinoline-7-sulfonamide oxalate (1:2)

1.5 ml of acetic acid are added to a suspension of 0.45 g (0.0014 mol) of N-[3-(diethylamino)propyl]-1,2,3,4-tetrahydroisoquinoline-7-sulfonamide and 0.149 g (0.0014 mol) of benzaldehyde in 12 ml of tetrahydrofuran. The suspension is stirred for 1 hour at ambient temperature and then 0.14 g (0.0021 mol) of sodium cyanoborohydride was added. The mixture was stirred overnight. The mixture is concentrated to dryness and the residue is treated with water and washed with ethyl ether. The aqueous phase is basified to pH=10 and is extracted several times with ethyl ether. The organic phases are combined and dried over anhydrous magnesium sulfate. The oil obtained is purified by silica gel column chromatography, with a dichloromethane/methanol (95:5) mixture used as eluant. The desired product (0.13 g; 22%) is obtained in the form of an oil.

The above oil is dissolved in 5 ml of ethanol, and then 0.06 g (0.0007 mol) of oxalic acid, dissolved in 5 ml of ethanol, is added. The precipitate is filtered off and washed with cold ethanol. 0.12 g of the desired product is obtained as a white solid.

Yield: 63%
Mp=91-103° C.
$^1$H-NMR (DMSO-$d_6$)δ(ppm): 7.5-7.1 (8H, m), 3.52 (2H, d), 2.9-2.5 (14H, m), 1.5 (2H, m), 0.9 (6H, t).

EXAMPLE 6

N-[3-(Diethylamino)propyl]-N-methyl-1,2,3,4-tetrahydroisoquinoline-7-sulfonamide hydrochloride

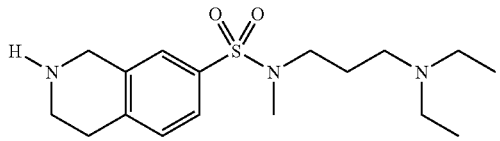

6.1-N-[2-(3-Diethylaminopropyl)-N-methyl-2-(2,2,2-trifluoroacetyl)-1,2,3,4-tetrahydroisoquinoline-7-sulfonamide 0.09 g (0.0022 mol) of a dispersion of sodium hydride (60%) in a mineral oil is added to a solution of 0.91 g (0.0021 mol) of N-[2-(3-diethylaminopropyl)-2-(2,2,2-trifluoroacetyl)-1,2,3,4-tetrahydroisoquinoline-7-sulfonamide (obtained according to the method described in stage 5.1- of Example 5) in 17 ml of dimethylformamide, cooled to 0° C. The mixture is stirred for one hour and 0.60 g (0.0042 mol) of methyl iodide is added. The mixture is stirred overnight at ambient temperature, and the solution is concentrated to dryness. The residue is treated with water. The aqueous phase is extracted several times with ethyl acetate. The organic phases are combined and dried over anhydrous magnesium sulfate. The oil obtained after filtration and evaporation of the solvent is purified by silica gel column chromatography, with a dichloromethane/methanol (95:5) mixture used as eluant, to give 0.31 g of the desired product in the form of an oil.

Yield: 34%
Mp=Oil

6.2-N-[2-(3-Diethylaminopropyl)-N-methyl-1,2,3,4-tetrahydroisoquinoline-7-sulfonamide To a solution of 0.20 g (0.00046 mol) of N-[2-(3-diethylaminopropyl)-N-methyl-2-(2,2,2-trifluoroacetyl)-1,2,3,4-tetrahydroisoquinoline-7-sulfonamide dissolved in 10 ml of methanol saturated with hydrogen chloride is heated for twelve hours at 60° C. The solution is concentrated to dryness and the residue is treated with water. The aqueous phase is extracted several times with ethyl ether. The organic phases are combined and dried over anhydrous magnesium sulfate, and the solution is concentrated to dryness, to give 0.02 9 of the desired product in the form of an oil.

Yield: 12%
Mp=Oil
$^1$H-NMR (DMSO)δ(ppm): 9.67 (1H, s, NH), 7.7 (1H, s), 7.68 (1H, d), 7.5 (1H, d), 4.4 (2H, s), 3.5-2.9 (12H, m), 2.7 (3H, s), 1.9 (2H, m), 1.15 (6H, t).

EXAMPLE 7

2-Cyclohexyl-N-[3-(diethylamino)propyl]-1,2,3,4-tetrahydroisoquinoline-7-sulfonamide ethanodioate (1:1)

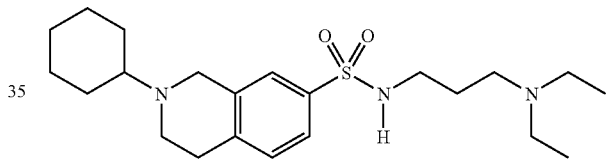

5 ml of acetic acid are added to a suspension of 1.70 g (0.0050 mol) of N-[3-(diethylamino)propyl]-1,2,3,4-tetrahydroisoquinoline-7-sulfonamide (obtained according to the method described in stage 3.2- of Example 3) and 0.98 g (0.0014 mol) of cyclohexanone in 50 ml of tetrahydrofuran. The mixture is stirred for 3 hours at ambient temperature and 0.47 g (0.0075 mol) of sodium cyanoborohydride is added. The mixture is stirred overnight. The mixture is concentrated to dryness. The residue is treated with water and washed with ethyl ether. The aqueous phase is basified to pH=10 and is extracted several times with ethyl ether. The organic phases are combined and dried over anhydrous magnesium sulfate. The oil obtained is purified by silica gel column chromatography, with a dichloromethane/methanol (95:5) mixture used as eluant. The desired product (0.22 g; 11%) is obtained in the form of an oil.

The above oil is dissolved in 5 ml of ethanol, and then a solution of 0.11 g (0.0012 mol) of oxalic acid, dissolved in 5 ml of ethanol, is added. The precipitate is filtered off and washed with cold ethanol. 0.32 g of the desired product is obtained as a white solid.

Yield: 97%
Mp=76-83° C.

¹H-NMR (DMSO-d₆)δ(ppm): 7.6 (2H, m), 7.4 (1 H, m), 4.2 (2H, s), 3.3 (H, m), 3.0 ( H, m), 2.7 (H, m), 2.4 (H, m), 2.0 (H, m), 1.7 (H, m), 1.4 (H, m), 1.1 (H, m).

EXAMPLE 8

1-Aminopropylpyrroline

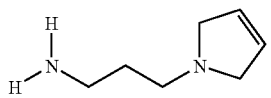

8.1-1-(2-Cyanoethyl)pyrroline 0.95 ml (0.0014 mol) of acrylonitrile is added, at 0° C., to a solution of 1.00 g (0.0014 mol) of pyrroline in methanol. The mixture is stirred overnight at ambient temperature and is concentrated to dryness, to give 1.65 g of the desired product in the form of an oil.
Yield: 93%
Mp=Oil

8.2-1-(3-Aminopropyl)pyrroline 0.024 g of 1M diisobutylaluminum hydride in toluene is added to a solution of 1.00 g (0.0089 mol) of 1-(2-cyanoethyl) pyrroline in 20 ml of dichloromethane. The mixture is stirred overnight at ambient temperature. The solution is treated with sodium sulfate decahydrate. The mixture is stirred for half an hour. The inorganic phases are filtered and the filtrate is concentrated to dryness, so as to obtain 1.00 g of a colorless oil.
Yield: 97%
Mp=Oil
¹H-NMR (CD₃Cl)δ(ppm): 5.75 (2H, s), 3.47 (4H, s), 2.75 (2H, t), 2.56 (2H, t), 1.69 (2H, q).

The table below illustrates the chemical structures and the physical properties of some compounds according to the invention. The elemental microanalyses and the NMR, IR or mass spectra confirm the structures of the compounds obtained.

In the table, for the compounds of formula I, "Mp." corresponds to the melting point.

TABLE 1

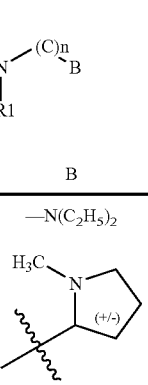

I

| No. | R2 | —(C)n— | R1 | B | Mp. (°C.) | salt |
|---|---|---|---|---|---|---|
| 1. | H | —(CH₂)₃— | H | —N(C₂H₅)₂ | 97–102 | Hydrochloride |
| 2. | H | —(CH₂)₂— | H | 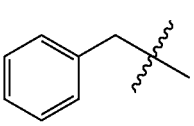 | 209–212 | Hydrochloride |
| 3. | CH₃ | —(CH₂)₃— | H | —N(C₂H₅)₂ | 58–62 | Oxalate |
| 4. | H | —(CH₂)₃— | CH₃ | —N(C₂H₅)₂ | amorphous | Hydrochloride |
| 5. | 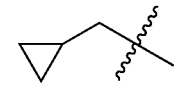 | —(CH₂)₃— | H | —N(C₂H₅)₂ | 91–95 | Oxalate |
| 6. | 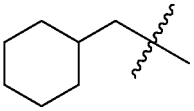 | —(CH₂)₃— | H | —N(C₂H₅)₂ | 98–103 | Oxalate |
| 7. | 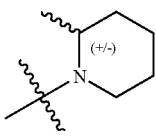 | —(CH₂)₃— | H | —N(C₂H₅)₂ | 144–147 | Oxalate |
| 8. | H | —(CH₂)₃— | H | (piperidinyl, +/-) | 65–70 | Hydrochloride |

TABLE 1-continued
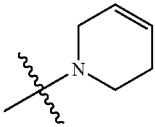
I
| No. | R2 | —(C)n— | R1 | B | Mp. (°C.) | salt |
|---|---|---|---|---|---|---|
| 9. | H | —(CH$_2$)$_3$— | H | 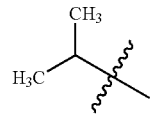 | >250 | Hydrochloride |
| 10 | 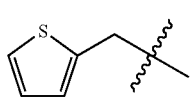 | —(CH$_2$)$_3$ | H | —N(C$_2$H$_5$)$_2$ | 54–59 | Oxalate |
| 11. | 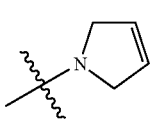 | —(CH$_2$)$_3$ | H | —N(C$_2$H$_5$)$_2$ | 109–115 | Oxalate |
| 12. | H | —(CH$_2$)$_3$ | H | —N(C$_2$H$_5$)$_2$ | 89–95 | Oxalate |
| 13. | H | —(CH$_2$)$_3$— | H | 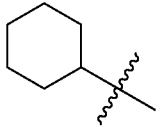 | 228–231 | Hydrochloride |
| 14. | 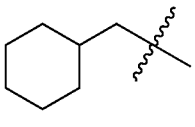 | —(CH$_2$)$_3$— | H | —N(C$_2$H$_5$)$_2$ | 55–60 | Oxalate |
| 15. | 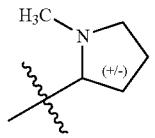 | —(CH$_2$)$_2$— | H | 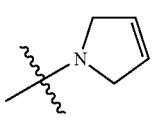 | 142–148 | Oxalate |
| 16. | —CH$_3$ | —(CH$_2$)$_3$— | H | 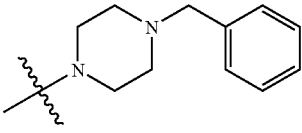 | 99–104 | Oxalate |
| 17. | H | —(CH$_2$)$_3$— | H | 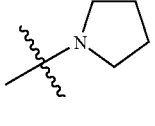 | 244–249 | Hydrochloride |
| 18. | H | —(CH$_2$)$_3$— | H | 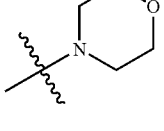 | 237–241 | Hydrochloride |
| 19. | H | —(CH$_2$)$_3$— | H |  | 238–245 | Hydrochloride |
| 20. | H | —(CH$_2$)$_3$— | H | —N(CH$_3$)$_2$ | 230–234 | Hydrochloride |

TABLE 1-continued

I: R2-N(tetrahydroisoquinoline)-SO2-N(R1)-(C)n-B

| No. | R2 | —(C)n— | R1 | B | Mp. (°C.) | salt |
|---|---|---|---|---|---|---|
| 21. | cyclohexyl-CH2- | —(CH2)3— | H | pyrrolidin-1-yl | 130–141 | Oxalate |
| 22. | cyclopropyl-CH2- | —(CH2)2— | H | 1-methylpyrrolidin-2-yl (+/−) | 50–60 | Oxalate |
| 23. | phenyl-CH2- | —(CH2)2— | H | 1-methylpyrrolidin-2-yl (+/−) | 77–82 | Oxalate |
| 24. | 4-isopropylphenyl-CH2- | —(CH2)2— | H | 1-methylpyrrolidin-2-yl (+/−) | 103–110 | Oxalate |
| 25. | benzo[1,3]dioxol-5-yl-CH2- | —(CH2)2— | H | 1-methylpyrrolidin-2-yl (+/−) | 106–109 | Oxalate |
| 26. | H | —(CH2)2— | H | 1-methylpyrrolidin-2-yl (+/−) | 114–117 | Hydrochloride |
| 27. | H | —(CH2)2— | H | 1-methylpyrrolidin-2-yl (+/−) | 115–117 | Hydrochloride |
| 28. | cyclohexyl-CH2- | —(CH2)2— | H | 1-methylpyrrolidin-2-yl (+/−) | 134–140 | Oxalate |
| 29. | cyclohexyl-CH2- | —(CH2)2— | H | 1-methylpyrrolidin-2-yl (+/−) | 133–138 | Oxalate |

TABLE 1-continued

| No. | R2 | —(C)n— | R1 | B | Mp. (°C.) | salt |
|---|---|---|---|---|---|---|
| 30. | 4-bromobenzyl | —(CH$_2$)$_2$— | H | (±)-1-methylpyrrolidin-2-yl | 86–110 | Oxalate |
| 31. | 2,5-dimethoxybenzyl | —(CH$_2$)$_2$— | H | (±)-1-methylpyrrolidin-2-yl | 87–90 | Oxalate |
| 32. | isobutyl (3-methylbutyl) | —(CH$_2$)$_2$— | H | (±)-1-methylpyrrolidin-2-yl | 66–77 | Oxalate |
| 33. | 3-methoxybenzyl | —(CH$_2$)$_2$— | H | (±)-1-methylpyrrolidin-2-yl | 80–107 | Oxalate |
| 34. | 3,5-dimethylbenzyl | —(CH$_2$)$_2$— | H | (±)-1-methylpyrrolidin-2-yl | 121–125 | Oxalate |

The compounds of the invention of formula I were subjected to pharmacological assays which showed their advantage as active substances in therapeutics.

More particularly, the compounds of the invention are histamine H$_3$-receptor antagonists. H$_3$ receptors are known to those skilled in the art and their advantage in therapeutics has been described in the literature ("Histamine H$_3$ receptor antagonists" Exp. Opinion Ther. Patents (2000) 10 (7) :1045-1055). Thus, the compounds of the invention of formula I were subjected to an in vitro affinity assay on the native histamine H$_3$ receptor in an adult rat brain membrane preparation, by specific binding of [$^3$H]—N-α-methylhistamine to this receptor, according to the methods described by A. Korte et al., in Biochem. Biophys. Res. Commun. 168, 979-986 (1990) and by R. E. West Jr. et al., in Mol. Pharmacol. 38, 610-613(1990).

The K$_i$ values for the compounds of the invention with respect to H$_3$ receptors are between 0.1 nM and 5.0 μM, and, more particularly, (+/−)-2-(cyclohexylmethyl)-N-[2-(1-methylpyrrolidin-2-yl)ethyl]-1,2,3,4-tetrahydroisoquinoline-7-sulfonamide (compound 15; Table 1) has a Ki of 0.3 nM.

The compounds of the invention of formula I were also subjected to a cAMP formation assay, on the human histamine H$_3$ receptor transfected into CHO cells, by inhibition of the agonism caused by the specific binding of R-α-methylhistamine to this receptor, according to the methods described by T. W. Lovenberg et al., in J. Pharmacol. Exp. Ther. 293, 771-778(2000).

The IC$_{50}$ values for the compounds of the invention with respect to H$_3$ receptors are between 0.1 nM and 5.0 μM.

By way of example, compound 15, included in Table 1, has an IC$_{50}$<10 nM, using an EIA kit (Amersham) to measure cAMP formation, on the human histamine H$_3$ receptor transfected into CHO cells, by inhibition of the agonism caused by the specific binding of R-α-methylhistamine to this receptor.

The compounds according to the invention have an activity that is selective for the histamine H$_3$ receptor. Effectively, the compounds have a Ki of greater than 7.0 μM in the in vitro affinity assay on the native histamine H$_1$ receptor in an adult rat brain membrane preparation by specific binding of [³H]-pirilamine to this receptor, according to the method described by Y. Q. Liu et al., in J. Pharmacol. Exp. Ther. 268, 959 (1994).

Furthermore, the compounds of the invention of formula I were subjected to in vivo tests showing their ability to reduce food intake in rats fasting for 24 h.

The experiments were carried out on Wistar rats. The rats were placed individually in transparent plastic cages 48×26, 5×21.5 cm. These cages were placed in a room insulated against any noise, at a temperature of 20 to 22° C., with a light cycle from 7 o'clock in the morning to 7 o'clock in the evening, the rats having free access to water and to the food.

Before the experiment was carried out, the rats were made to fast for 24 h, with access, however, to water ad libitum. On the day of the experiment, the carrier or the compound according to the present invention was administered i.p. or p.o., 15 or 30 minutes before a known amount of food (30 g) was made available. Each hour, for 6 hours, the amount of food ingested by the rat was measured.

It was shown that the $AD_{50}$ values (mg/kg i.p. or p.o.) for the compounds of the invention with respect to food intake may be less than 10. For example, (+/−)-2-(4-isopropylbenzyl)-N-[2-(1-methylpyrrolidin-2-yl)ethyl]-1,2,3,4-tetrahydroisoquinoline-7-sulfonamide (compound 24; Table 1) decreases food intake by 54% during the first hour after the i.p. administration of 10 mg/kg of the product.

The results of the tests show that the compounds of the invention make it possible to reduce food intake in animals. Thus, they make it possible to control weight gain, to treat obesity or to aid weight loss, in animals, but also in humans.

Thus, according to another of its aspects, a subject of the invention is medicaments which comprise a compound of formula I or an addition salt of the latter with a pharmaceutically acceptable acid or else a hydrate or a solvate of the compound of formula I.

These medicaments find their use in therapeutics, in particular in the treatment of pathologies in which a histamine $H_3$-receptor antagonist provides a therapeutic benefit. In particular, such pathologies are obesity and diabetes. In addition, these compounds may be used in the treatment of central nervous system diseases such as vigilance and sleep disorders, narcolepsy, Alzheimer's disease and other dementias, Parkinson's disease, attention disorders in hyperkinetic children, memory and learning disorders, epilepsy, schizophrenia, moderate cognitive disorders, depression and anxiety. The states of depression and anxiety include, for example, anxieties of anticipatory type (before a surgical procedure, before a dental treatment, etc), anxiety caused by alcohol or drug dependency or withdrawal, mania, seasonal affective disorders, migraines and nausea. They can also be used in the treatment of sexual dysfunction, dizziness and travel sickness.

The use of the compounds according to the invention for the preparation of a medicament for use in treating the pathologies mentioned above is an integral part of the invention.

According to another of its aspects, the present invention relates to pharmaceutical compositions comprising, as active ingredient, at least one compound according to the invention. These pharmaceutical compositions contain an effective dose of at least one compound according to the invention, or a pharmaceutically acceptable salt, a hydrate or a solvate of said compound, and also at least one or more pharmaceutically acceptable excipients. Said excipients are chosen according to the pharmaceutical form and the method of administration desired, from the usual excipients that are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula I above, or possible salt, solvate or hydrate thereof, can be administered in unit administration form, as a mixture with conventional pharmaceutical excipients, to animals or to human beings for the prophylaxis or the treatment of the disorders or of the diseases above.

The appropriate unit administration forms comprise oral administration forms, such as tablets, soft or hard gelatin capsules, powders, granules and oral solutions or suspensions, sublingual, buccal, intratracheal or intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

In order to obtain the desired prophylactic or therapeutic effect, the dose of active ingredient can range between 0.1 μg and 50 mg per kg of bodyweight and per day. Each unit dose can contain from 0.1 to 1000 mg, preferably from 1 to 500 mg, of active ingredient in combination with a pharmaceutical excipient. This unit dose can be administered 1 to 5 times a day so as to administer a daily dose of from 0.5 to 5000 mg, preferably from 1 to 2500 mg.

There may be specific cases were higher or lower dosages are appropriate. Such dosages also belong to the invention. According to the usual practice, the dosage appropriate for each patient is determined by the physician according to the method of administration and the weight and response of said patient.

By way of example, a unit administration form of a compound according to the invention:

| | |
|---|---:|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

According to another of its aspects, the present invention also relates to a method of treating the pathologies indicated above, which comprises the administration, to a patient, of an effective dose of a compound according to the invention or a pharmaceutically acceptable salt or hydrate or solvate thereof.

What is claimed is:
1. A compound of formula I:

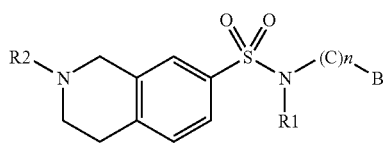

in which:

n represents a value from 1 to 6;

—(C)n- represents a $C_{1-6}$ alkylidene group optionally substituted with 1 to 4 substituents selected from halogen, hydroxyl, nitro, cyano, amino, $C_{1-3}$ monoalkylamino, $C_{2-6}$ dialkylamino and $C_{1-3}$ alkoxy;

R1 represents
a hydrogen atom, or
a $C_{1-6}$ alkyl group;

R2 represents
a hydrogen atom, or
a $C_{1-6}$ alkyl or $C_{3-6}$ cycloalkyl group optionally substituted with 1 to 4 substituents selected from a halogen atom, a hydroxyl, nitro, cyano, amino, $C_{1-3}$ monoalkylamino, $C_{2-6}$ dialkylamino, $C_{1-2}$ perhaloalkyl, $C_{1-3}$ haloalkyl, $C_{1-3}$ alkoxy, $C_{3-6}$ cycloalkyl, a monocyclic heteroaryl, and an aryl; the aryl being optionally substituted with 1 to 4 substituents selected from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl, $C_{1-3}$ alkoxy and a $C_{1-3}$ alkylidenedioxy group;

B represents NR3R4, wherein
R3 and R4 represent, independently of one another, a $C_{1-6}$ alkyl group, or a hydrogen atom; or
R3 and R4 together represent a $C_{1-6}$ alkylidene group, a $C_{2-8}$ alkenylidene group, a $C_{1-3}$ alkylidene-O—$C_{1-3}$ alkylidene group, or a $C_{1-3}$ alkylidene-N(R5)-$C_{1-3}$ alkylidene group where R5 represents a hydrogen atom, or a $C_{1-3}$ alkyl or $C_{1-6}$ alkylcarbonyl group, it being possible for these $C_{1-3}$ alkyl and $C_{1-6}$ alkylcarbonyl groups to be substituted with a halogen atom, or a hydroxyl, $C_{1-3}$ alkoxy, nitro, cyano or amino group; or B represents an aminocycle, linked via a carbon to the group —NR1-(C)n-, said aminocycle being selected from aziridine, azetidine, pyrrolidine, piperidine and morpholine; the groups R3 and R4 and also the aminocycle being optionally substituted with 1 to 4 substituents selected from a phenyl, a benzyl, a halogen, a hydroxyl, a nitro, cyano, amino, $C_{1-3}$ monoalkylamino, $C_{2-6}$ dialkylamino, $C_{1-3}$ alkyl and $C_{1-3}$ alkoxy group; the nitrogen atom being optionally substituted with a $C_{1-3}$ alkyl;

or a salt, a hydrate or a solvate thereof;
with the exclusion of the compound in which $R_1$ and $R_2$ represent hydrogen atoms, B represents a dimethylamino group and —(C)n- represents an ethylidene group.

2. A compound as claimed in claim 1 wherein:
n is equal to 2, 3 or 4; and
R1 represents a hydrogen atom or a $C_{1-2}$ alkyl group; and
R2 represents a hydrogen atom, or a $C_{1-4}$ alkyl or $C_{5-6}$ cycloalkyl group optionally substituted with 1 to 4 substituents selected from a phenyl, a $C_{3-6}$ cycloalkyl, $C_{1-2}$ perhaloalkyl, $C_{1-3}$ haloalkyl and $C_{1-3}$ alkoxy; the phenyl being optionally substituted with 1 to 4 substituents selected from a halogen atom, hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl, $C_{1-3}$ alkoxy group and $C_{1-3}$ alkylidenedioxy; and B represents NR3R4, wherein
R3 and R4 represent, independently of one another, a $C_{1-4}$ alkyl group; or
when R3 and R4 together represent a $C_{1-6}$ alkylidene group, a $C_{2-8}$ alkenylidene group, a $C_{1-3}$ alkylidene-O—$C_{1-3}$ alkylidene group or a $C_{1-3}$ alkylidene-N(R5)-$C_{1-3}$ alkylidene group, B represents a group:

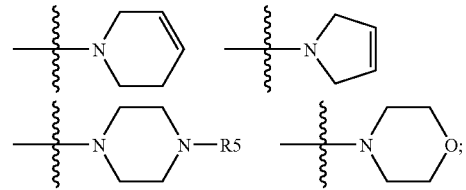

or B represents an aminocycle linked via a carbon to the group —NR1-(C)n, chosen from aziridine, azetidine, pyrrolidine, piperidine and morpholine;
the groups R3, R4 and R5 and also the aminocycle being optionally substituted;
or a salt, a hydrate or a solvate thereof.

3. A compound as claimed in claim 2, wherein, when B represents NR3R4 and R3 and R4 together form a $C_{1-6}$ alkylidene group, a $C_{2-8}$ alkenylidene group, a $C_{1-3}$ alkylidene-O—$C_{1-3}$ alkylidene group or a $C_{1-3}$ alkylidene-N(R5)—$C_{1-3}$ alkylidene group, or when B represents an aminocycle, then B is selected from the group consisting of:

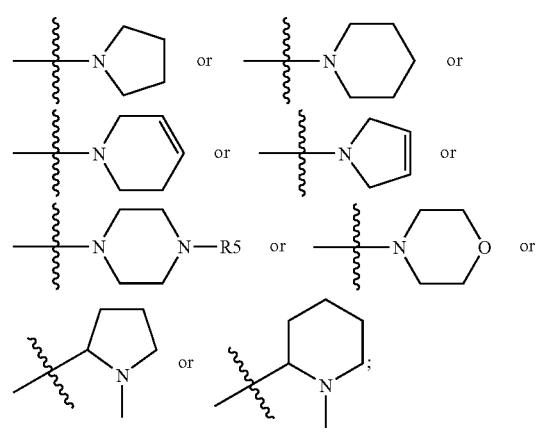

or a salt, a hydrate or a solvate thereof.

4. A compound as claimed in claim 1, selected from the group consisting of:
N-[3-(diethylamino)propyl]-1,2,3,4-tetrahydroisoquinoline-7-sulfonamide;
(+/−)-N-[2-(1-methylpyrrolidin-2-yl)ethyl]-1,2,3,4-tetrahydroisoquinoline-7-sulfonamide;
N-[3-(diethylamino)propyl]-2-methyl-1,2,3,4-tetrahydroisoquinoline-7-sulfonamide;
N-[3-(diethylamino)propyl]-N-methyl-1,2,3,4-tetrahydroisoquinoline-7-sulfonamide;
2-benzyl-N-[3-(diethylamino)propyl]-1,2,3,4-tetrahydroisoquinoline-7-sulfonamide;
2-(cyclopropylmethyl)-N-[3-(diethylamino)propyl]-1,2,3,4-tetrahydroisoquinoline-7-sulfonamide;
2-(cyclohexylmethyl)-N-[3-(diethylamino)propyl]-1,2,3,4-tetrahydroisoquinoline-7-sulfonamide;
(+/−)-N-[3-(2-methylpiperidin-1-yl)propyl]-1,2,3,4-tetrahydroisoquinoline-7-sulfonamide;
N-[3-(3,6-dihydropyridin-1(2H)-yl)propyl]-1,2,3,4-tetrahydroisoquinoline-7-sulfonamide;
N-[3-(diethylamino)propyl]-2-isopropyl-1,2,3,4-tetrahydroisoquinoline-7-sulfonamide;
N-[3-(diethylamino)propyl]-2-(2-thienylmethyl)-1,2,3,4-tetrahydroisoquinoline-7-sulfonamide;

N-[3-(diethylamino)propyl]-2-(3-thienylmethyl)-1,2,3,4-tetrahydroisoquinoline-7-sulfonamide;

N-[3-(2,5-dihydro-1H-pyrrol-1-yl)propyl]-1,2,3,4-tetrahydroisoquinoline-7-sulfonamide;

2-cyclohexyl-N-[3-(diethylamino)propyl]-1,2,3,4-tetrahydroisoquinoline-7-sulfonamide;

(+/−)-2-(cyclohexylmethyl)-N-[2-(1-methylpyrrolidin-2-yl)ethyl]-1,2,3,4-tetrahydroisoquinoline-7-sulfonamide;

N-[3-(2,5-dihydro-1H-pyrrol-1-yl)propyl]-2-methyl-1,2,3,4-tetrahydroisoquinoline-7-sulfonamide;

N-[3-(4-benzylpiperazin-1-yl)propyl]-1,2,3,4-tetrahydroisoquinoline-7-sulfonamide;

N-(3-pyrrolidin-1-ylpropyl)-1,2,3,4-tetrahydroisoquinoline-7-sulfonamide;

N-(3-morpholin-4-ylpropyl)-1,2,3,4-tetrahydroisoquinoline-7-sulfonamide;

N-[3-(dimethylamino)propyl]-1,2,3,4-tetrahydroisoquinoline-7-sulfonamide;

2-(cyclohexylmethyl)-N-(3-pyrrolidin-1ylpropyl)-1,2,3,4-tetrahydroisoquinoline-7-sulfonamide;

(+/−)-2-(cyclopropylmethyl)-N-[2-(1-methylpyrrolidin-2-yl)ethyl]-1,2,3,4-tetrahydroisoquinoline-7-sulfonamide;

(+/−)-2-benzyl-N-[2-(1-methylpyrrolidin-2-yl)ethyl]1,2,3,4-tetrahydroisoquinoline-7-sulfonamide;

(+/−)-2-(4-isopropylbenzyl)-N-[2-(1-methylpyrrolidin-2-yl)ethyl]-1,2,3,4-tetrahydroisoquinoline-7-sulfonamide;

(+/−)-2-(1,3-benzodioxo1-5-ylmethyl)-N-[2-(1-methylpyrrolidin-2-yl)ethyl]-1,2,3,4-tetrahydroisoquinoline-7-sulfonamide;

(+)-N-[2-(1-methylpyrrolidin-2-yl)ethyl]-1,2,3,4-tetrahydroisoquinoline-7-sulfonamide;

(−)-N-[2-(1-methylpyrrolidin-2-yl)ethyl]-1,2,3,4-tetrahydroisoquinoline-7-sulfonamide;

(+)-2-(cyclohexylmethyl)-N-[2-(1-methylpyrrolidin-2-yl)ethyl]-1,2,3,4-tetrahydroisoquinoline-7-sulfonamide;

(−)-2-(cyclohexylmethyl)-N-[2-(1-methylpyrrolidin-2-yl)ethyl]-1,2,3,4-tetrahydroisoquinoline-7-sulfonamide;

(+/−)-2-(4-bromobenzyl)-N-[2-(1-methylpyrrolidin-2-yl)ethyl]-1,2,3,4-tetrahydroisoquinoline-7-sulfonamide;

(+/−)-2-(2,5-dimethoxybenzyl)-N-[2-(1-methylpyrrolidin-2-yl)ethyl]-1,2,3,4-tetrahydroisoquinoline-7-sulfonamide;

(+/−)-2-(2-methylbutyl)-N-[2-(1-methylpyrrolidin-2-yl)ethyl]-1,2,3,4-tetrahydroisoquinoline-7-sulfonamide;

(+/−)-2-(3-methoxybenzyl)-)-N-[2-(1-methylpyrrolidin-2-yl)ethyl]-1,2,3,4-tetrahydroisoquinoline-7-sulfonamide; and (+/−)-2-(3,5-dimethylbenzyl)-N-[2-(1-methylpyrrolidin-2-yl)ethyl]-1,2,3,4-tetrahydroisoquinoline-7-sulfonamide;

or a salt, a hydrate or a solvate thereof.

5. The compound according to claim 1 which is (+)-N-[2-(1-methylpyrrolidin-2-yl)ethyl]-1,2,3,4-tetrahydroisoquinoline-7-sulfonamide; or a salt, solvate or hydrate thereof.

6. The compound according to claim 1 which is (−)-N-[2-(1-methylpyrrolidin-2-yl)ethyl]-1,2,3,4-tetrahydroisoquinoline-7-sulfonamide; or a salt, solvate or hydrate thereof.

7. A compound of formula I:

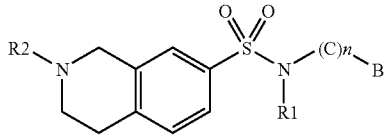

in which:

n represents a value from 1 to 6;

—(C)n- represents a $C_{1-6}$ alkylidene group optionally substituted with 1 to 4 substituents selected from halogen, hydroxyl, nitro, cyano, amino, $C_{1-3}$ monoalkylamino, $C_{2-6}$ dialkylamino and $C_{1-3}$ alkoxy;

R1 represents a hydrogen atom, or a $C_{1-6}$ alkyl group;

R2 represents a $C_{1-6}$ alkyl or $C_{3-6}$ cycloalkyl group optionally substituted with 1 to 4 substituents selected from a halogen atom, a hydroxyl, nitro, cyano, amino, $C_{1-3}$ monoalkylamino, $C_{2-6}$ dialkylamino, $C_{1-2}$ perhaloalkyl, $C_{1-3}$ haloalkyl, $C_{1-3}$ alkoxy, $C_{3-6}$ cycloalkyl, a monocyclic heteroaryl, and an aryl; the aryl being optionally substituted with 1 to 4 substituents selected from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl, $C_{1-3}$ alkoxy and a $C_{1-3}$ alkylidenedioxy group;

B represents NR3R4, wherein R3 and R4 represent, independently of one another, a $C_{1-6}$ alkyl group, or a hydrogen atom; or R3 and R4 together represent a $C_{1-6}$ alkylidene group, a $C_{2-8}$ alkenylidene group, a $C_{1-3}$ alkylidene-O—$C_{1-3}$ alkylidene group, or a $C_{1-3}$ alkylidene-N(R5)-$C_{1-3}$ alkylidene group where R5 represents a hydrogen atom, or a $C_{1-3}$ alkyl or $C_{1-6}$ alkylcarbonyl group, it being possible for these $C_{1-3}$ alkyl and $C_{1-6}$ alkylcarbonyl groups to be substituted with a halogen atom, or a hydroxyl, $C_{1-3}$ alkoxy, nitro, cyano or amino group;

or B represents an aminocycle, linked via a carbon to the group -NR1-(C)n-, said aminocycle being selected from aziridine, azetidine, pyrrolidine, piperidine and morpholine;

the groups R3 and R4 and also the aminocycle being optionally substituted with 1 to 4 substituents selected from a phenyl, a benzyl, a halogen, a hydroxyl, a nitro, cyano, amino, $C_{1-3}$ monoalkylamino, $C_{2-6}$ dialkylamino, $C_{1-3}$ alkyl and $C_{1-3}$ alkoxy group; the nitrogen atom being optionally substituted with a $C_{1-3}$ alkyl;

or a salt, a hydrate or a solvate thereof.

8. The compound according to claim 7 which is (+)-2-(cyclohexylmethyl)-N-[2-(1-methylpyrrolidin-2-yl)ethyl]-1,2,3 ,4-tetrahydroisoquinoline-7-sulfonamide; or a salt, solvate or hydrate thereof.

9. The compound according to claim 7 which is (−)-2-(cyclohexylmethyl)-N-[2-(1-methylpyrrolidin-2-yl)ethyl]-1,2,3 ,4-tetrahydroisoquinoline-7-sulfonamide; or a salt, solvate or hydrate thereof.

10. A compound selected from the group consisting of (+)-2-(cyclohexylmethyl)-N-[2-(1-methylpyrrolidin-2-yl)ethyl] -1,2,3 ,4-tetrahydroisoquinoline-7-sulfonamide and (−)-2-(cyclohexylmethyl)-N-[2-(1-methylpyrrolidin-2-yl)ethyl] -1,2,3 ,4-tetrahydroisoquinoline-7-sulfonamide; or a salt of said compound; or a hydrate of said salt.

11. A pharmaceutical composition containing a compound of formula I, as claimed in claim 1, or a salt, solvate or hydrate thereof, and at least one pharmaceutical excipient.

12. A pharmaceutical composition comprising a compound according to claim 2, or a salt, solvate or hydrate thereof, and at least one pharmaceutical excipient.

13. A pharmaceutical composition comprising a compound according to claim 3, or a salt, solvate or hydrate thereof, and at least one pharmaceutical excipient.

14. A pharmaceutical composition comprising a compound according to claim 4, or a salt, solvate or hydrate thereof, and at least one pharmaceutical excipient.

15. A pharmaceutical composition comprising a compound according to claim 5, or a salt, solvate or hydrate thereof, and at least one pharmaceutical excipient.

16. A pharmaceutical composition comprising a compound according to claim 6, or a salt, solvate or hydrate thereof, and at least one pharmaceutical excipient.

17. A pharmaceutical composition comprising a compound according to claim 7, or a salt, solvate or hydrate thereof, and at least one pharmaceutical excipient.

18. A pharmaceutical composition comprising a compound according to claim 8, or a salt, solvate or hydrate thereof, and at least one pharmaceutical excipient.

19. A pharmaceutical composition comprising a compound according to claim 9, or a salt, solvate or hydrate thereof, and at least one pharmaceutical excipient.

* * * * *

UNITED STATES PATENT AND TRADEMARK OFFICE
CERTIFICATE OF CORRECTION

PATENT NO. : 7,833,999 B2
APPLICATION NO. : 11/569929
DATED : November 16, 2010
INVENTOR(S) : Juan Antonio Diaz Martin et al.

It is certified that error appears in the above-identified patent and that said Letters Patent is hereby corrected as shown below:

In column 7, line 6, delete "N,N,N',N' tetramethylazodicarboxamide," and insert -- N,N,N',N'-tetramethylazodicarboxamide, --, therefor.

In column 8, line 55, delete "(2H, m)" and insert -- (2H, m), --, therefor.

In column 10, line 24, delete "2-Benzyi-" and insert -- 2-Benzyl- --, therefor.

In column 12, line 13, delete "0.02 9" and insert -- 0.02 g --, therefor.

In column 15-16, line 5, No. 10, delete "-(CH$_2$)$_3$" and insert -- -(CH$_2$)$_3$- --, therefor.

In column 15-16, line 6, No. 11, delete "-(CH$_2$)$_3$" and insert -- -(CH$_2$)$_3$- --, therefor.

In column 15-16, line 7, No. 12, delete "H" and insert -- 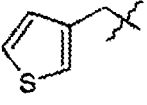 --, therefor.

In column 15-16, line 7, No. 12, delete "-(CH$_2$)$_3$" and insert -- -(CH$_2$)$_3$- --, therefor.

In column 17-18, line 9, No. 26, delete " 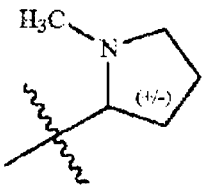 " and insert -- 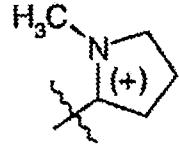 --, therefor.

Signed and Sealed this
Twentieth Day of September, 2011

David J. Kappos
*Director of the United States Patent and Trademark Office*

CERTIFICATE OF CORRECTION (continued)

U.S. Pat. No. 7,833,999 B2

In column 17-18, line 10, No. 27, delete " 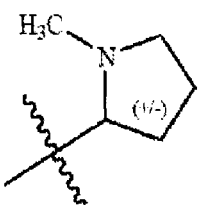 " and insert -- 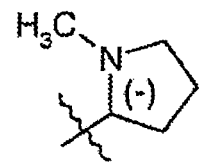 --, therefor.

In column 17-18, line 11, No. 28, delete " 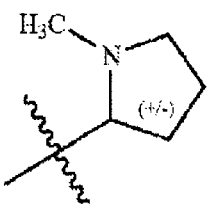 " and insert -- 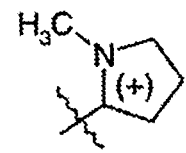 --, therefor.

In column 17-18, line 11, No. 28, delete "134-1" and insert -- 134-140 --, therefor.

In column 17-18, line 12, No. 29, delete " 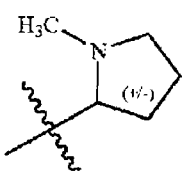 " and insert -- 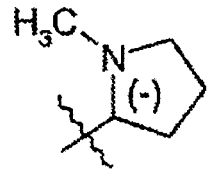 --, therefor.

In column 21, line 2, delete "pirilamine" and insert -- pyrilamine --, therefor.

In column 23, line 47, in claim 2, delete "$C_{1-2}$" and insert -- $C_{1-2}$ --, therefor.

In column 23, line 51, in claim 2, delete "$C_{1-3}$" and insert -- $C_{1-3}$ --, therefor.

In column 25, line 28-29, in claim 4, delete "ethyl]1,2,3,4-" and insert -- ethyl]-1,2,3,4- --, therefor.

In column 26, line 15, in claim 7, delete "$C_{2-6}$" and insert -- $C_{2-6}$ --, therefor.

In column 26, line 19, in claim 7, delete "$C_{1-3}$" and insert -- $C_{1-3}$ --, therefor.

In column 26, line 21, in claim 7, delete "$C_{3-6}$" and insert -- $C_{3-6}$ --, therefor.

In column 26, line 24, in claim 7, delete "$C_{1-3}$" and insert -- $C_{1-3}$ --, therefor.

In column 26, line 52-53, in claim 8, delete "ethyl] -1,2,3 ,4-" and insert -- ethyl]-1,2,3,4- --, therefor.

In column 26, line 56-57, in claim 9, delete "ethyl] -1,2,3 ,4-" and insert -- ethyl]-1,2,3,4- --, therefor.

In column 26, line 61, in claim 10, delete "ethyl] -1,2,3 ,4-" and insert -- ethyl]-1,2,3,4- --, therefor.

In column 26, line 63, in claim 10, delete "ethyl] -1,2,3 ,4-" and insert -- ethyl]-1,2,3,4- --, therefor.